United States Patent
Swain

(10) Patent No.: US 8,894,620 B2
(45) Date of Patent: Nov. 25, 2014

(54) ACTIVATION OF BONE AND CARTILAGE FORMATION

(75) Inventor: Larry D. Swain, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 3 days.

(21) Appl. No.: 13/414,224

(22) Filed: Mar. 7, 2012

(65) Prior Publication Data

US 2012/0165766 A1 Jun. 28, 2012

Related U.S. Application Data

(63) Continuation of application No. 12/147,097, filed on Jun. 26, 2008, now Pat. No. 8,152,783.

(60) Provisional application No. 60/937,904, filed on Jun. 29, 2007.

(51) Int. Cl.
*A61M 1/00* (2006.01)

(52) U.S. Cl.
USPC ............ 604/290; 604/319; 604/42; 601/6; 602/42; 602/50; 424/426; 424/447

(58) Field of Classification Search
USPC ............ 604/290, 319; 606/151; 623/23.58
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |

(Continued)

FOREIGN PATENT DOCUMENTS

| AU | 550575 A1 | 8/1982 |
|---|---|---|
| AU | 745271 | 4/1999 |

(Continued)

OTHER PUBLICATIONS

N. A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Vy Q. Bui

(57) ABSTRACT

Provided is a method of activating osteogenic or chondrogenic activity at a site in a subject in need thereof. Also provided is a method of treating a bone or cartilage defect in a subject. Additionally, the use of a reduced pressure apparatus for treating a bone or cartilage defect adjacent to dura mater, periosteum, or endosteum is provided. Further provided is a composition for treating a bone or cartilage defect. Also, the use of a reduced pressure apparatus and a biocompatible scaffold for the manufacture of a composition for treating a bone or cartilage defect adjacent to dura mater, periosteum or endosteum is provided.

16 Claims, 13 Drawing Sheets

(56) References Cited

U.S. PATENT DOCUMENTS

| | | |
|---|---|---|
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,717,030 A * | 2/1998 | Dunn et al. ............... 523/111 |
| 6,071,267 A | 6/2000 | Zamierowski |
| 6,135,116 A | 10/2000 | Vogel et al. |
| 6,235,061 B1 * | 5/2001 | Laurencin et al. ......... 623/23.57 |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0225347 A1 * | 12/2003 | Argenta et al. ............... 601/6 |
| 2003/0236573 A1 | 12/2003 | Evans et al. |
| 2006/0204442 A1 | 9/2006 | Tapolsky et al. |
| 2007/0032762 A1 | 2/2007 | Vogel |
| 2008/0275409 A1 | 11/2008 | Kane et al. |

FOREIGN PATENT DOCUMENTS

| | | |
|---|---|---|
| AU | 455496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

(56) References Cited

OTHER PUBLICATIONS

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

\* cited by examiner

C

Granulation tissue

Periosteum
Cortical bone

Cortical bone

A

B

A

B

ACTIVATION OF BONE AND CARTILAGE FORMATION

CROSS-REFERENCE TO RELATED APPLICATIONS

This application is a continuation of U.S. patent application Ser. No. 12/147,097, filed Jun. 26, 2008 now U.S. Pat. No. 8,152,783, entitled "Activation of Bone and Cartilage Formation", which claims the benefit of U.S. Provisional Application No. 60/937,904, filed Jun. 29, 2007, incorporated by reference.

BACKGROUND

1. Field of the Invention

The present invention relates generally to tissue treatment systems and in particular to a system and method for promoting the growth of new bone or cartilage tissue by activating dura mater, periosteum or endosteum through the application of reduced pressure.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifolding device. The porous pad contains cells or pores that are capable of distributing reduced pressure to the tissue and channeling fluids that are drawn from the tissue. The porous pad often is incorporated into a dressing having other components that facilitate treatment.

Wound healing may be broadly split into three overlapping basic phases: inflammation, proliferation, and maturation. The inflammatory phase is characterized by hemostasis and inflammation. The next phase consists mainly of angiogenesis, granulation tissue formation, collagen deposition and epithelialization. The final phase includes maturation and remodeling. The complexity of the wound healing process is augmented by the influence of local factors such as ischemia, edema, and infection, as well as systemic factors such as diabetes, age, hypothyroidism, malnutrition, and obesity. The rate limiting step of wound healing, however, is often angiogenesis.

In bone and cartilage healing, the periosteum is the primary source of precursor cells that develop into osteoblasts and chondroblasts. The bone marrow, endosteum, small blood vessels and fibrous connective tissue are secondary sources of precursor cells. However, bone and, especially, cartilage healing is often slow and frequently inadequate. For this reason, the medical community has long sought to develop improved methods of tissue repair and replacement for bone and cartilage defects.

With craniofacial defects, successful repair or replacement is greatly compromised without the endogenous osteogenic capacity of the dura mater. Unfortunately, dura mater in humans begins to lose its osteogenic capacity rapidly after humans reach about two years of age. Current reconstructive techniques for craniofacial defects use autogenous, allogeneic, and prosthetic materials to counter the osteogenic deficiency of mature dura mater. Growth factors also are commonly used to facilitate tissue regeneration. These techniques may achieve some functional restoration of craniofacial defects, but all are inherently limited by factors such as donor-site morbidity, unpredictable graft resorption, insufficient autogenous resources, viral disease transmission, immunologic incompatibility, structural failure, unsatisfactory aesthetic results, and cost. Moreover, it has been shown that osteoblasts induced by growth factors are initially derived from undifferentiated mesenchymal stem cells of the dura mater, and later, though limited, augmented by cells in the overlying connective tissue rather than from cells in the cranial bone surrounding the defect. Cytokines or other factors are required to induce bone forming cells derived from the dura and the overlying connective tissue.

Methods that improve healing of bone and cartilage are thus desired. The present invention addresses that need.

SUMMARY

The problems presented by existing methods for bone and cartilage healing are solved by the systems and methods of the illustrative embodiments described herein. In one embodiment, a method is provided that includes activating osteogenic or chondrogenic activity at a site in a subject in need thereof. The method comprises applying reduced pressure to the dura mater, periosteum or endosteum at the site in the subject.

In another embodiment, a method is provided that includes treating a bone or cartilage defect in a subject. The method comprises applying reduced pressure to the dura mater, periosteum or endosteum that is adjacent to the defect.

In a further embodiment, the use of a reduced pressure apparatus for treating a bone or cartilage defect adjacent to dura mater, periosteum, or endosteum is provided.

In still another embodiment, a composition for treating a bone or cartilage defect is provided. The composition comprises a reduced pressure apparatus and a biocompatible scaffold. With this composition, the defect is adjacent to dura mater, periosteum or endosteum.

In a still further embodiment, the use of a reduced pressure apparatus and a biocompatible scaffold for the manufacture of a composition for treating a bone or cartilage defect adjacent to dura mater, periosteum or endosteum is provided.

Other objects, features, and advantages of the illustrative embodiments will become apparent with reference to the drawings and detailed description that follow.

DETAILED DESCRIPTION OF ILLUSTRATIVE EMBODIMENTS

Figure 1:
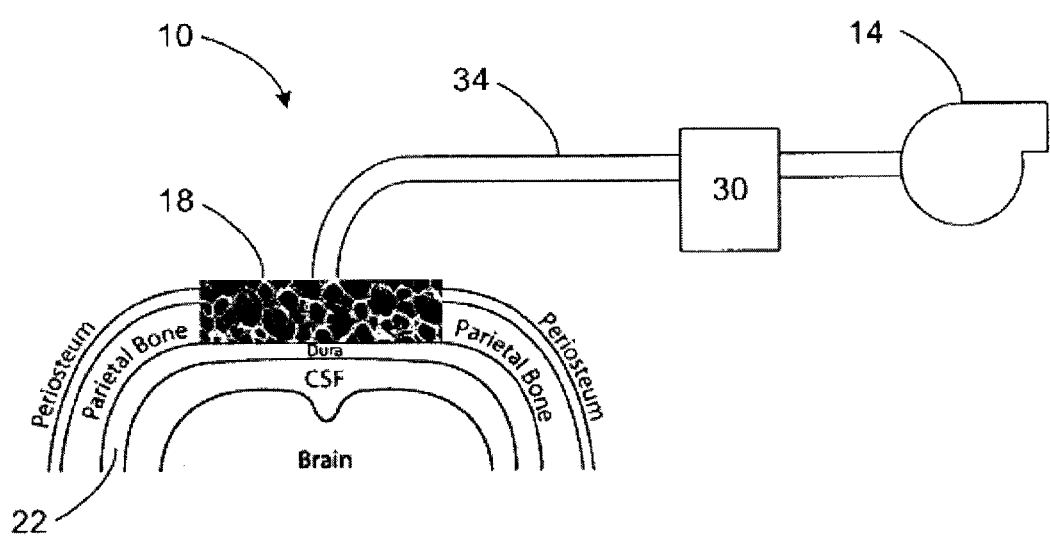
FIG. 1 is a schematic diagram of a tissue scaffold applied to a cranial defect such that the tissue scaffold is in contact with a dura mater.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

In the context of this specification, the term "reduced pressure" generally refers to a pressure that is less than the ambient pressure at a tissue site that is subjected to treatment. In most cases, this reduced pressure will be less than the atmospheric pressure of the location at which the patient is located. Although the terms "vacuum" and "negative pressure" may be used to describe the pressure applied to the tissue site, the actual pressure applied to the tissue site may be significantly greater than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure. Various methods and compositions describing reduced pressure treatment of tissue is described in the following patent publications: WO08042481A2, WO08036361A2, WO08036359A2, WO08036162A2, WO08013896A2, WO07143060A2, WO07133556A2, WO07133555A2, WO07106594A2, WO07106592A2, WO07106591A2, WO07106590A2, WO07106589A2, WO07092397A2, WO07067685A2, WO05033273A2, WO05009488A2, WO04105576A2, WO04060148A2, WO03092620A2, WO03018098A2, WO0061206A1, WO0038755A2, US20070123895, U.S. Pat. No. 7,351,250, U.S. Pat. No. 7,346,945, U.S. Pat. No. 7,316,672, U.S. Pat. No. 7,279,612, U.S. Pat. No. 7,214,202, U.S. Pat. No. 7,186,244, U.S. Pat. No. 7,108,683, U.S. Pat. No. 7,077,832, U.S. Pat. No. 7,070,584, U.S. Pat. No. 7,004,915, U.S. Pat. No. 6,994,702, U.S. Pat. No. 6,951,553, U.S. Pat. No. 6,936,037, U.S. Pat. No. 6,856,821, U.S. Pat. No. 6,814,079, U.S. Pat. No. 6,767,334, U.S. Pat. No. 6,695,823 and U.S. Pat. No. 6,135,116.

This application is based on the discovery that the utilization of reduced pressure on a bone or cartilage adjacent to dura mater, periosteum or endosteum causes induction of bone or cartilage formation by the dura mater (where the defect is a craniofacial defect), the periosteum or the endosteum. The application of a foam dressing to the bone or cartilage can also induce new bone or cartilage formation, but not to the extent of reduced pressure treatment. See Examples.

Thus, in some embodiments, the application is directed to a method of activating osteogenic or chondrogenic activity at a site in a subject in need thereof. The method comprises applying reduced pressure to the dura mater, periosteum or endosteum at the site in the subject. Preferably, the subject has a bone or cartilage defect adjacent to the dura mater, the periosteum or the endosteum. However, the application is not limited to sites of bone or cartilage defects. The subjects may, for example, be treated with these methods on the intact dura mater, periosteum or endosteum where there is no defect, and the resultant new tissue transplanted to defect sites elsewhere in the body.

In some embodiments, the reduced pressure is applied to the dura mater. In other embodiments, the reduced pressure is applied to the periosteum. As shown in Example 4, endosteum fluid flow in an intact bone is increased by a short exposure of the periosteum to reduced pressure. It is believed that this increased fluid flow in the endosteum is indicative of increased osteogenic activity in the endosteum. Thus, endosteum osteogenic activity can be induced by applying reduced pressure to the periosteum.

In additional embodiments, the reduced pressure is applied to the endosteum. Such a treatment would be useful, e.g., where applying reduced pressure to a gap in a bone to induce osteogenesis into a scaffold placed in the gap.

These methods are not narrowly limited to the treatment of any particular type of defect. However, it is recognized that the predominant defects in subjects treated with these methods are defects (a) from a wound, (b) due to cancer, (c) due to a degenerative disease (e.g., osteoarthritis), or (d) congenital. In some embodiments, the defect is a bone defect. In other embodiments, the defect is a cartilage defect.

Preferably, a biocompatible scaffold is placed at the site. Where the site comprises a defect, the biocompatible scaffold is preferably inserted into the defect. The methods are not limited to the use of any particular biocompatible scaffold; numerous useful biocompatible scaffolds are known in the art. In some embodiments, the biocompatible scaffold is a bioresorbable polymer. In preferred embodiments, the bioresorbable polymer is a polylactide-coglycolide (PLAGA) polymer or a polyethylene glycol-PLAGA copolymer.

The biocompatible scaffold can also include components that facilitate wound healing. Such components include cytokines, e.g., those that promote angiogenesis or cell growth such as vascular endothelial growth factor (VEGF), basic fibroblast growth factor (bFGF), platelet derived growth factor (PDGF), angiogenin, angiopoietin-1, granulocyte colony-stimulating factor (G-CSF), hepatocyte growth factor/scatter factor (HGF/SF), interleukin-8 (IL-8), placental growth factor, platelet-derived endothelial cell growth factor (PD-ECGF), platelet-derived growth factor-BB (PDGF-BB), transforming growth factor-α (TGF-α), transforming growth factor-β (TGF-β), tumor necrosis factor-α (TNF-α), vascular endothelial growth factor (VEGF), or a matrix metalloproteinase (MMP). Other components that can usefully be included in the scaffold include antibiotics, or cells that are capable of becoming osteoblasts, chondroblasts, or vascular tissue, such as embryonic stem cells, adult hematopoietic stem cells, bone marrow stromal cells, or mesenchymal stem cells. The cells may optionally be genetically engineered to express a useful protein, such as one of the above cytokines.

In preferred embodiments, the reduced pressure is applied to the defect through a manifold connected to a reduced pressure source, where the manifold is porous and is placed on or in the defect. It is also preferred that the manifold is from a flowable material that is delivered through a manifold delivery tube to the tissue site such that the flowable material fills the defect. In some embodiments, the manifold is a bioresorbable polymer and is capable of serving as a biocompatible scaffold. Non-limiting examples of such a bioresorbable polymer include a polylactide-coglycolide (PLAGA) polymer or a polyethylene glycol-PLAGA copolymer.

FIG. 1 shows a preferred example of is method as applied to a defect adjacent to the dura mater. It is noted that the same reduced pressure system can be utilized with periosteum or endosteum.

Referring to FIG. 1, describing a non-limiting embodiment of the instant application, a system 10 is provided that includes a reduced pressure source 14 fluidly connected to a manifold 18 that is placed adjacent to and in contact with dura mater 22. The manifold 18 may include any biocompatible material that is capable of distributing the reduced pressure supplied by the reduced pressure source 14 to the dura mater 22. The manifold 18 may be formed from a porous material or may include flow channels that assist in distributing reduced pressure. In one embodiment, the manifold 18 may include a scaffold or the entire manifold may be a scaffold that is capable of supporting the growth and integration of new tissue. The scaffold may be incorporated within the new tissue growth and remain in place following repair or regeneration of new tissue. The scaffold may be formed from a bioabsorbable substance that is absorbed by the body following tissue repair or regeneration.

A canister 30 may be fluidly connected between the reduced pressure source 14 and the manifold 18 to trap and hold tissue exudates and other fluids that are withdrawn from areas adjacent the manifold 18 during the application of reduced pressure. Filters may be fluidly connected between the manifold 18 and the reduced pressure source 14 to prevent contamination of the reduced pressure source 14 by tissue fluids and bacteria. Preferably, the fluid connection between the reduced pressure source 14 and the manifold 18 (and any other fluid components) is provided by medical-grade conduit 34. The conduit 34 may be fluidly attached to the manifold 18 by a manifold adapter (not shown) or by placing an end of the conduit 34 directly in contact with the manifold 18 such that the conduit 34 communicates directly with the pores or fluid channels associated with the manifold 18.

In one embodiment, the manifold 18 is a bioabsorbable scaffold, and the reduced pressure source 14 supplies reduced pressure to the dura mater 22 through the conduit 34 and the scaffold. Without being bound by any particular mechanism of action, it is believed that the presence of reduced pressure above the dura mater 22 imparts a strain on the dura mater 22 that activates a phenotypic expression of the dura mater 22 that is similar to that seen in neonatal, immature dura mater. The stimulation of the dura mater itself by imposing a reduced pressure and strain on the dura mater is sufficient to populate a scaffold with new bone and supporting tissue. See Example 1.

The reduced pressure treatment is not narrowly limited to any particular time of application. Example 1 establishes that a one day (24 h) duration is sufficient to induce new bone formation, bridging of a defect gap, and significant scaffold infiltration. In various embodiments, the reduced pressure can be applied for anywhere from 0.1 h to 144 h or more. In other embodiments, the reduced pressure is applied for at least 24 h. In other examples, the reduced pressure is applied for less than 24 h, e.g. 12 h. In additional embodiments, the reduced pressure is applied for 12 h to 3 days.

As established in Examples 2 and 3, simply placing a foam manifold (preferably GranuFoam®) at a site of desired bone or cartilage growth (e.g., in a defect) on a periosteum or endosteum induces bone or cartilage growth, although the induction is not as great as with reduced pressure. Therefore, it is contemplated that a biocompatible foam may be advantageously placed on a defect adjacent to a dura mater, a periosteum or an endosteum without reduced pressure to induce bone or cartilage growth.

The present invention is also directed to a method of treating a bone or cartilage defect in a subject. The method comprises applying reduced pressure to the dura mater, periosteum or endosteum that is adjacent to the defect. In some embodiments, the reduced pressure is applied to the dura mater. In other embodiments, the reduced pressure is applied to the periosteum. In still other embodiments, the reduced pressure is applied to the endosteum.

As with the method described above, in this method a biocompatible scaffold is preferably inserted into the defect. The biocompatible scaffold is preferably a bioresorbable polymer, most preferably a polylactide-coglycolide (PLAGA) polymer or a polyethylene glycol-PLAGA copolymer.

In preferred embodiments, the reduced pressure is applied to the dura mater, periosteum or endosteum through a manifold connected to a reduced pressure source. Here, the manifold is porous and is placed on or in the defect. More preferably, the manifold is from a flowable material that is delivered through a manifold delivery tube to the tissue site such that the flowable material fills the defect. Even more preferably, the manifold comprises a bioresorbable polymer and is capable of serving as a biocompatible scaffold. The bioresorbable polymer that is most preferred is a polylactide-coglycolide (PLAGA) polymer or a polyethylene glycol-PLAGA copolymer.

In these methods, the reduced pressure can be applied for anywhere from 0.1 h to 144 h or more. In many embodiments, the reduced pressure is applied for at least 24 h.

The application is also directed to the use of a reduced pressure apparatus for treating a bone or cartilage defect adjacent to dura mater, periosteum, or endosteum. As with the methods described above, the reduced pressure apparatus preferably comprises a manifold connected to a reduced pressure source, wherein the manifold is porous and is placed on or in the defect. More preferably, the manifold is from a flowable material that is delivered through a manifold delivery tube to the tissue site such that the flowable material fills the defect.

In additional embodiments, the invention is directed to a composition for treating a bone or cartilage defect. The composition comprises a reduced pressure apparatus and a biocompatible scaffold, wherein the defect is adjacent to dura mater, periosteum or endosteum. Preferably, the biocompatible scaffold is a bioresorbable polymer, most preferably a polylactide-coglycolide (PLAGA) polymer or a polyethylene glycol-PLAGA copolymer.

In preferred compositions, the reduced pressure apparatus comprises a manifold connected to a reduced pressure source. The manifold in these embodiments is porous. Preferably, the manifold comprises the biocompatible scaffold. More preferably, the manifold comprises a bioresorbable polymer, most preferably a polylactide-coglycolide (PLAGA) polymer or a polyethylene glycol-PLAGA copolymer.

In these embodiments, the manifold is preferably from a flowable material that is delivered through a manifold delivery tube to the tissue site such that the flowable material fills the defect.

The application is further directed to the use of a reduced pressure apparatus and a biocompatible scaffold for the manufacture of a composition for treating a bone or cartilage defect adjacent to dura mater, periosteum or endosteum. Preferably, the biocompatible scaffold is a bioresorbable polymer, most preferably a polylactide-coglycolide (PLAGA) polymer or a polyethylene glycol-PLAGA copolymer.

For this use, the reduced pressure apparatus preferably comprises a manifold connected to a reduced pressure source, where the manifold is porous. More preferably, the manifold comprises the biocompatible scaffold. Even more preferably, the manifold comprises a bioresorbable polymer, most preferably a polylactide-coglycolide (PLAGA) polymer or a polyethylene glycol-PLAGA copolymer.

In preferred embodiments, the manifold is from a flowable material that is delivered through a manifold delivery tube to the tissue site such that the flowable material fills the defect.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

Stimulation of Osteogenic Activity in the Dura Mater with Reduced Pressure

Figure 2:
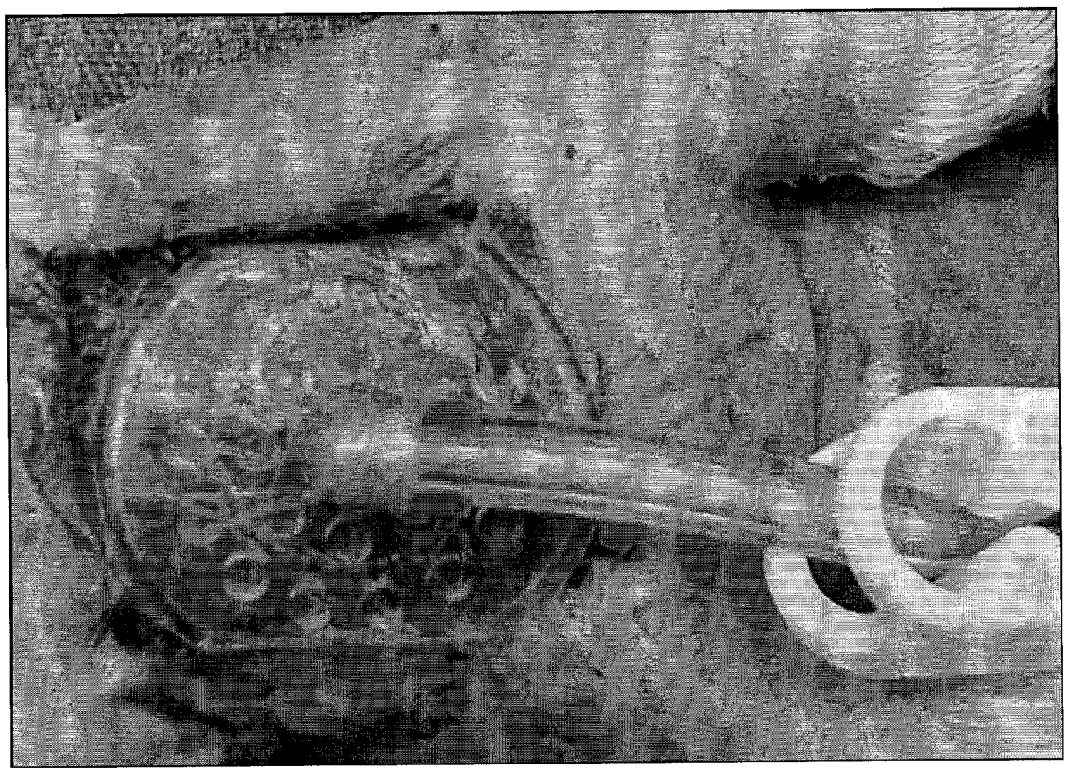
FIG. 2 is a photograph illustrating a bone induction system and method according to an embodiment of the present invention being applied to a rabbit cranium to induce new bone growth through osteogenic activation of intact dura mater.

Referring to FIG. 2, a cranial defect study was performed to evaluate the effects of applying reduced pressure to intact dura mater through a scaffold. Critical size defects were made in the cranium of a rabbit with dura mater left intact. A scaffold similar to that shown in FIG. 1 (i.e. manifold and/or scaffold 18) was placed in contact with the dura mater. Several tests were conducted that varied the amount of time over which reduced pressure was applied. A control test was run in which no reduced pressure was supplied to the scaffold placed in contact with the dura mater. Samples of the cranium and scaffold were examined following 12 weeks of in-life healing for each particular defect (inclusive of the amount of time over which reduced pressure was applied). The measured values included the amount of new bone area observed, the percentage of quantitative bridge assessment, the percentage of total scaffold infiltration, and new bone growth penetration into the upper half of the scaffold. These measurements are presented in Table 1 below.

TABLE 1

| Treatment | New Bone Area (mm$^2$) | Quantitative Bridging Assessment | Total Scaffold Infiltration | Upper-Half Scaffold Infiltration (mm$^2$) |
|---|---|---|---|---|
| Control (n = 8) | 3.76 | 55% | 8.9% | 0.36 |
| 24 hrs (n = 8) | 7.18 ($p \leq 0.011$) | 87% ($p \leq 0.027$) | 18.9% ($p \leq 0.0097$) | 1.74 ($p \leq 0.00021$) |
| 4 days (n = 8) | 6.90 ($p \leq 0.015$) | 82% ($p \leq 0.048$) | 17.9% ($p \leq 0.014$) | 1.79 ($p \leq 0.00076$) |
| 6 days (n = 8) | 7.64 ($p \leq 0.0032$) | 85% ($p \leq 0.040$) | 20.4% ($p \leq 0.0031$) | 2.30 ($p \leq 0.00023$) |
| 10 days (n = 7) | 6.98 ($p \leq 0.0066$) | 85% ($p \leq 0.040$) | 20.6% ($p \leq 0.0043$) | 2.34 ($p \leq 0.000013$) |

"New-Bone" is the total area of bone formed in the scaffold. "Bridging Assessment" is the percent of the defect bridged with bone from one side of the defect to the other, as measured through the center of the defect. The bridging assessment is an important clinical factor since it indicates the effectiveness of closing the defect. "Percent Scaffold Infiltration" is the percent of the total available space in the scaffold that is filled with bone. "Upper-Half Infiltration" is the amount of bone in the upper-half of the scaffold.

As Table 1 illustrates, application of reduced pressure significantly increased all bone formation parameters tested, relative to the control specimens. During the study, care was taken to maintain intact dura prior to insertion of the tissue scaffold. At each time point, reduced pressure stimulated statistically greater amounts of new bone deposition than the control, indicating that a threshold event was achieved after a single day of application. Although application for longer duration did not increase bridging assessments, longer duration did influence the distribution of bone deposition, particularly in the upper-half of the tissue scaffold that is further removed from the dura mater. Differences observed and quantified presumably relate to dural activation since the soft tissue above the defect was not subjected to reduced pressure.

Figure 3:
FIG. 3 is a micrograph of an animal specimen illustrating the normal architecture of a dural sheath in comparison to newly forming bone in a rabbit cranium subjected to reduced pressure according to certain embodiments of the invention.
Figure 4:
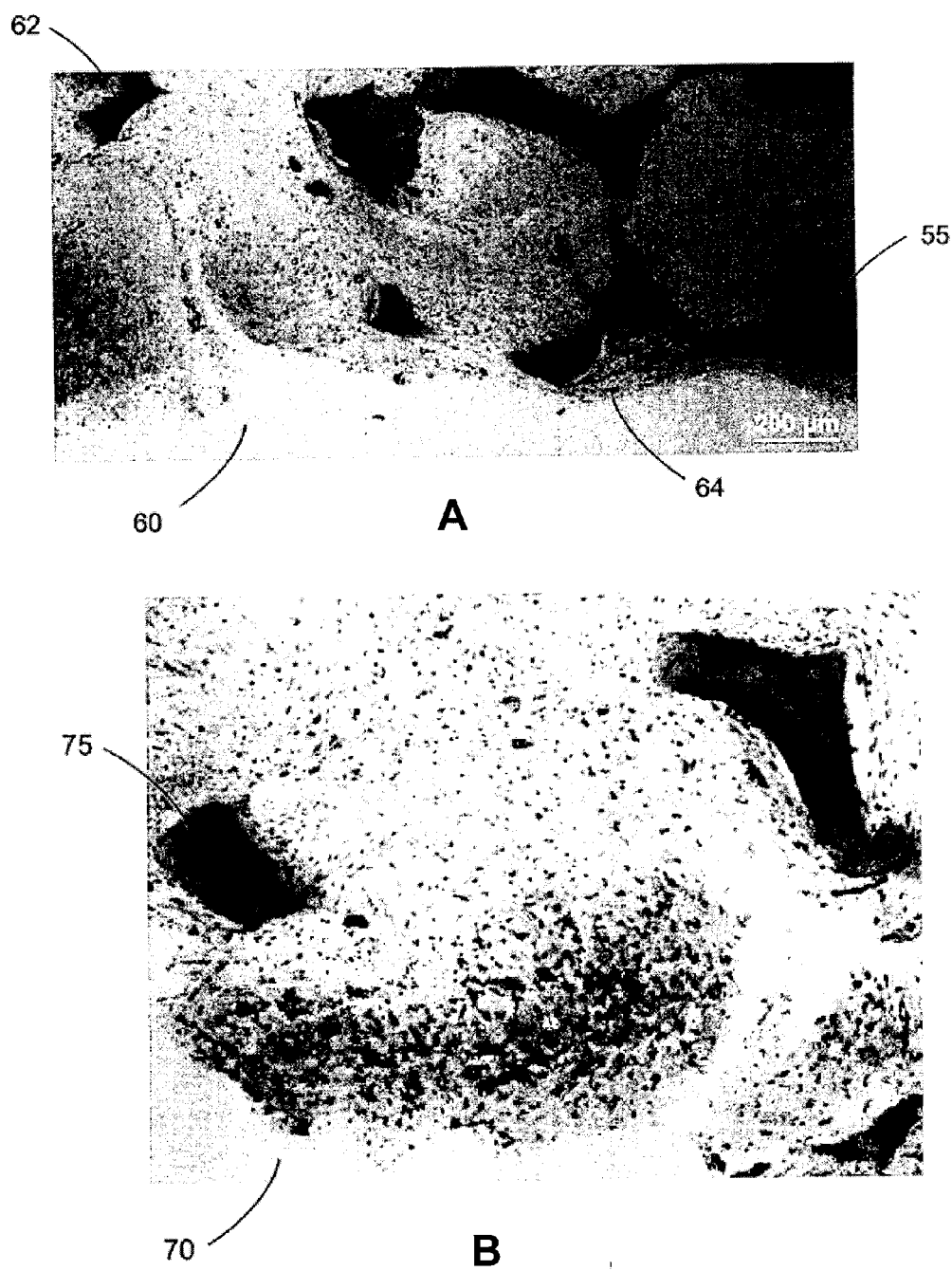
FIG. 4 is micrographs of experimental results. Panel A is a micrograph of an animal specimen illustrating the demarcation between areas of new bone formation and areas without new bone formation. Panel B is a micrograph of an animal specimen in which central nervous system tissue and a tissue scaffold are not separated by intact dura mater. Panel C is a micrograph of an animal specimen in which new bone formation is in intimate contact with intact dural membrane.
Figure 4:
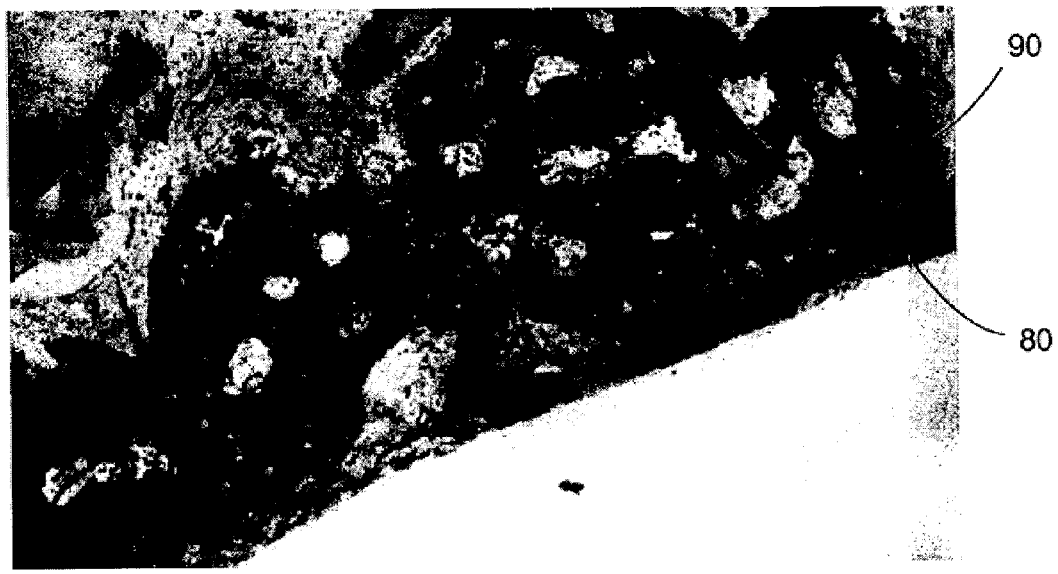

Referring to FIGS. 3-4C, micrographs were taken of specimens obtained in the tests described above. FIG. 3 illustrates a micrograph of a normal architecture of a dural sheath 40 adjacent to newly forming bone 45 in a rabbit cranium. Also present are osteoblasts 47 between the dural sheath 40 and new bone 45. Examination of new bone formation and integration into scaffold material subjected to reduced pressure confirms the influence of intact dura mater in the osteogenic response to the scaffold material. FIG. 4A is a micrograph of an animal specimen illustrating the sharp demarcation between areas of new bone formation 55 and areas without new bone formation 60. Although both areas contain scaffold material 62, the absence of intact dural membrane consistently correlates with the absence of new bone formation. In FIG. 4A, new bone formation 55 is located in proximity to an intact dural membrane 64. FIG. 4B illustrates a specimen in which central nervous system tissue 70 and a tissue scaffold 75 are not separated by intact dura mater. Noticeably absent from FIG. 4B is new bone formation. In contrast, FIG. 4C illustrates a well defined dural membrane 80 and a large amount of new bone formation 90 in intimate contact with the dural membrane 80.

Example 2

Stimulation of a Periosteum Osteogenic Response by Foam Manifolds and Reduced Pressure A foam manifold and reduced pressure were evaluated for their ability to induce the periosteum to synthesize new bone.

The intact, undamaged cranial periosteum of rabbits was exposed. A GranuFoam® (KCI Licensing, Inc., San Antonio Tex.) foam dressing was applied to the bone. In some treatments, the foam-covered bone was also subjected to reduced pressure. After treatment, the animals were sacrificed and the treated bone was subjected to paraffin embedding, sectioning and staining to evaluate the effect of the treatment on new bone formation.

Figure 5:
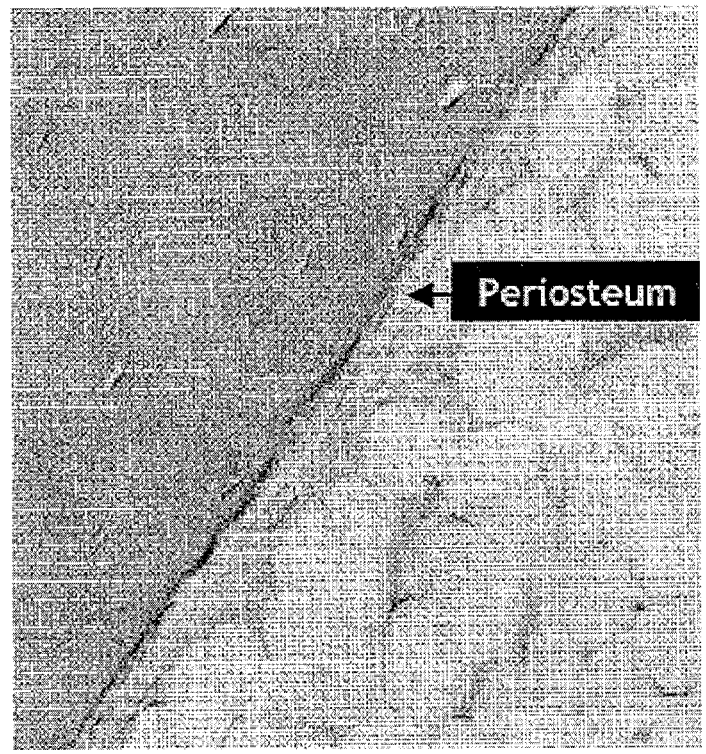
FIG. 5 is a micrograph of the surface of a naïve undamaged rabbit cranial bone.
Figure 6:
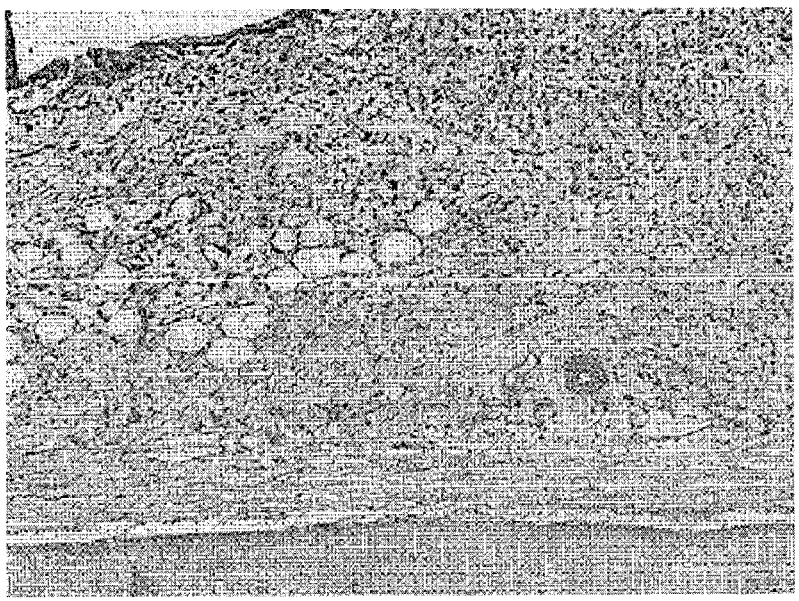
FIG. 6 is a micrograph of a bone that was in contact with GranuFoam® for six days without reduced pressure.
Figure 7:
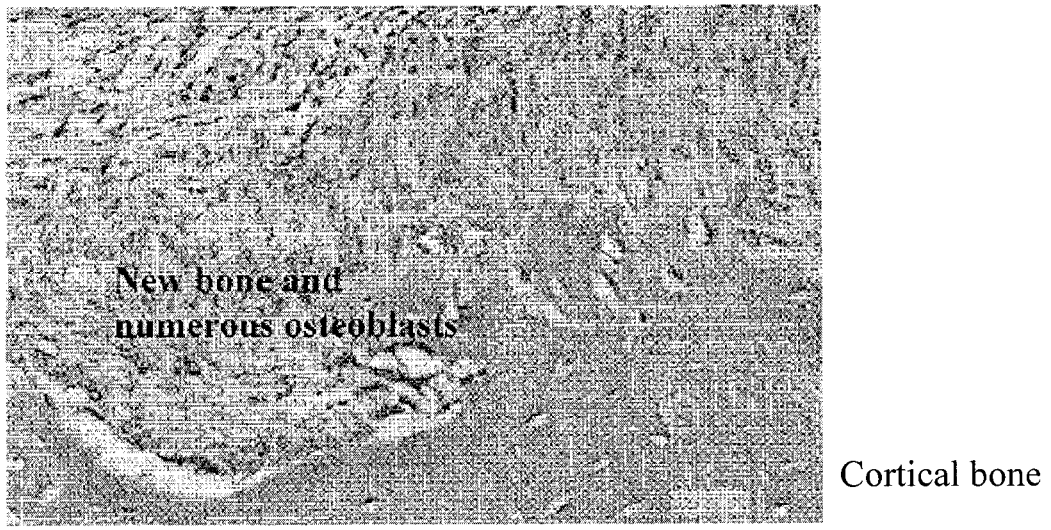
FIG. 7 is a micrograph of a bone that was in contact with GranuFoam® with reduced pressure for six days.
Figure 8:
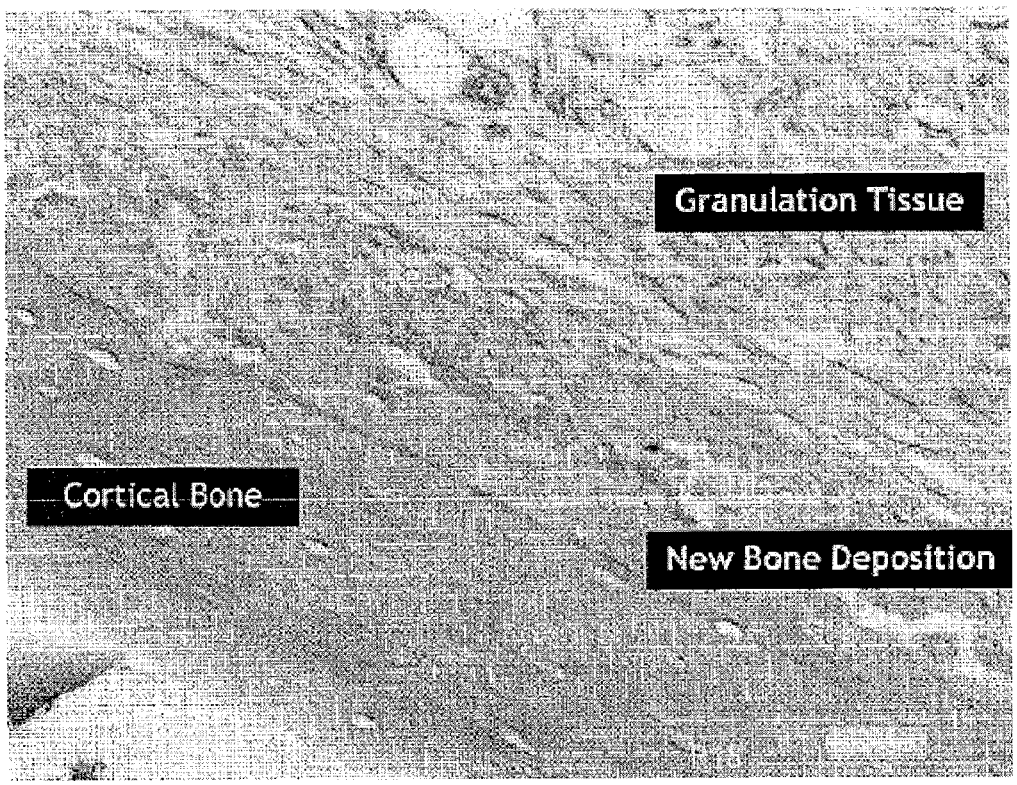
FIG. 8 is another micrograph of a bone that was in contact with GranuFoam® with reduced pressure for six days.

FIG. 5 shows a naïve, undamaged periosteum in a rabbit. The arrow denotes the location of the thin layer of the periosteum. The periosteum is thin and unremarkable. By contrast, FIG. 6 shows induction of granulation tissue overlying the periosteum where the foam was maintained in contact with the bony surface for 6 days without reduced pressure. Granulation tissue was induced by exposure of the bone to the foam without a reduced pressure treatment. This demonstrates foam induction of granulation tissue overlying the periosteum. FIG. 7 shows treatment of bone with foam and reduced pressure (−125 mm Hg). New bone formation was enhanced over the foam treatment alone. FIG. 8 shows another section of a bone subjected to foam and reduced pressure, showing new bone deposition under newly formed granulation tissue. The deposition of new bone overlies the original periosteal-cortical interface.

In conclusion, this Example shows the induction of new bone when foam alone is applied. More rapid and extensive bone formation occurs with application of reduced pressure through the foam.

Example 3

Induction of Cartilage Tissue Formation

Cartilage formation was observed in response to the application of reduced pressure therapy to the surface of intact cranial periosteal membranes. These observations are of significance in that cartilage formation in response to a therapy is unique and of great interest in the field of tissue engineering. These formations were observed in the absence of scaffold materials and only with the application of reduced pressure. No cartilage formation was observed in controls.

Cartilage degeneration caused by congenital abnormalities or disease and trauma is of great clinical consequence. Because of the lack of blood supply and subsequent wound-healing response, damage to cartilage generally results in an incomplete repair by the body. Full-thickness articular cartilage damage, or osteochondral lesions, allow for the normal inflammatory response, but result in inferior fibrocartilage formation. Surgical intervention is often the only option. Treatments for repair of cartilage damage are often less than satisfactory, and rarely restore full function or return the tissue to its native normal state. This Example demonstrates the induction of new cartilage from periosteum using GranuFoam® and reduced pressure treatment.

A foam manifold and reduced pressure were evaluated for their ability to induce the periosteum to synthesize new cartilage. The intact, undamaged crania of rabbits were exposed. A GranuFoam® (KCI Licensing, Inc., San Antonio Tex.) foam dressing was applied to the bone. With some treatments, the foam-covered bone was also subjected to reduced pressure. After treatment, the animals were sacrificed and the treated bone was subjected to paraffin embedding, sectioning and staining to evaluate the effect of the treatment on new bone formation.

Figure 9:
FIG. 9 is a micrograph of the surface of an undamaged bone, with superficial muscle tissue overlying the periosteum. The dots denote the demarcation between the cortical bone and the thin layer of the periosteum.
Figure 10:
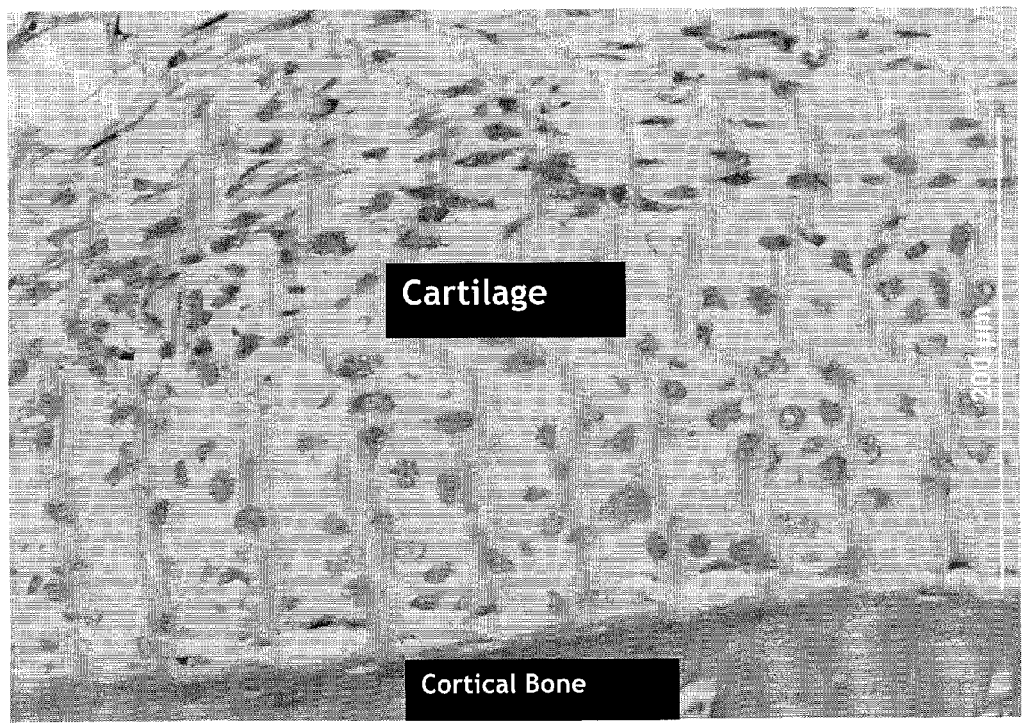
FIG. 10, panels A and B, is micrographs showing induction of cartilage tissue in response to contact with GranuFoam® and reduced pressure.
Figure 10:
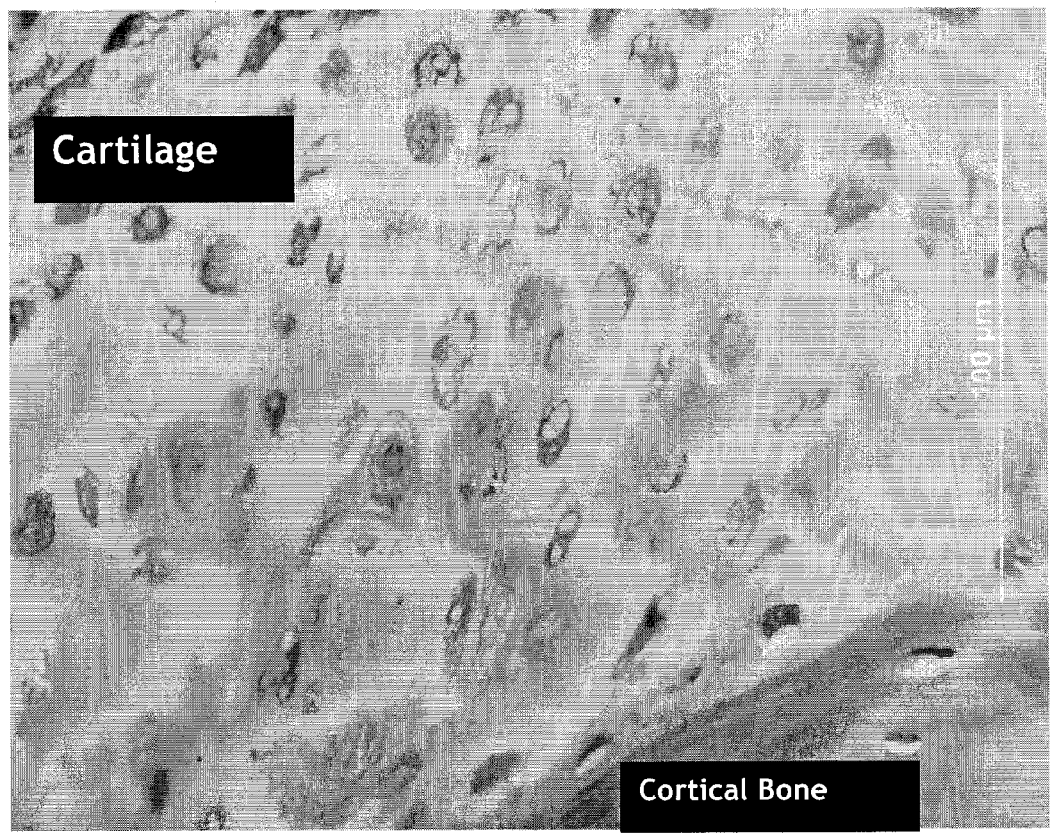

FIG. 9 shows a naïve, undamaged periosteum in rabbit cranium. The dots denote the demarcation between the cortical bone and the thin layer of the periosteum. By contrast, FIG. 10A, B show that, with the use of GranuFoam®) and reduced pressure (−125 mm Hg), extensive cartilage tissues was induced overlying the periosteum.

Example 4

Induction of Endosteal Activity

Figure 11:
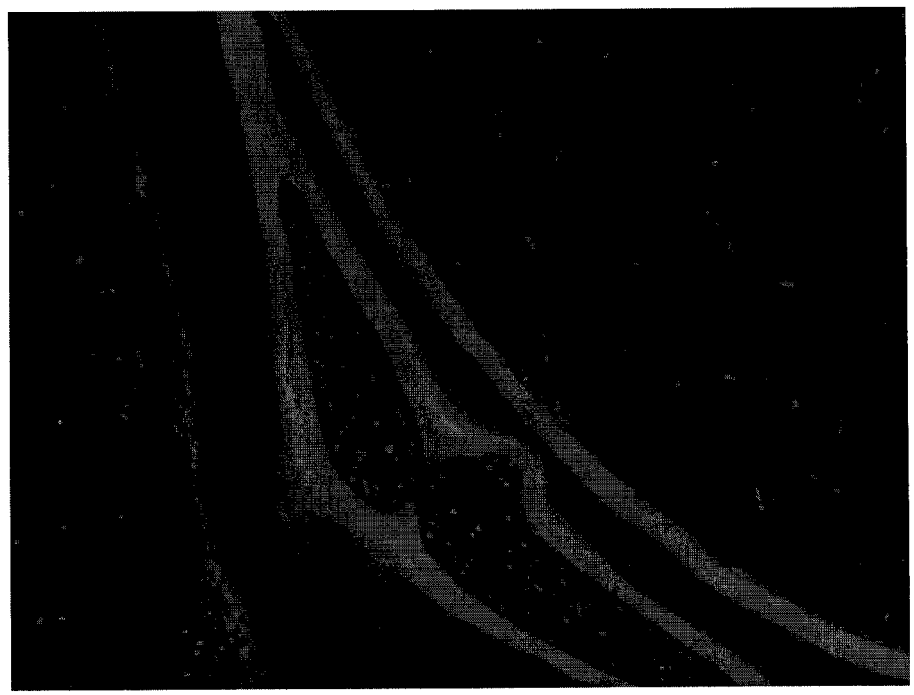
FIG. 11 is micrographs (10×) showing procion red staining of endosteal bone surfaces interfacing with marrow tissues, in a bone treated with reduced pressure through GranuFoam® (A) or an untreated contralateral control (B).
Figure 11:
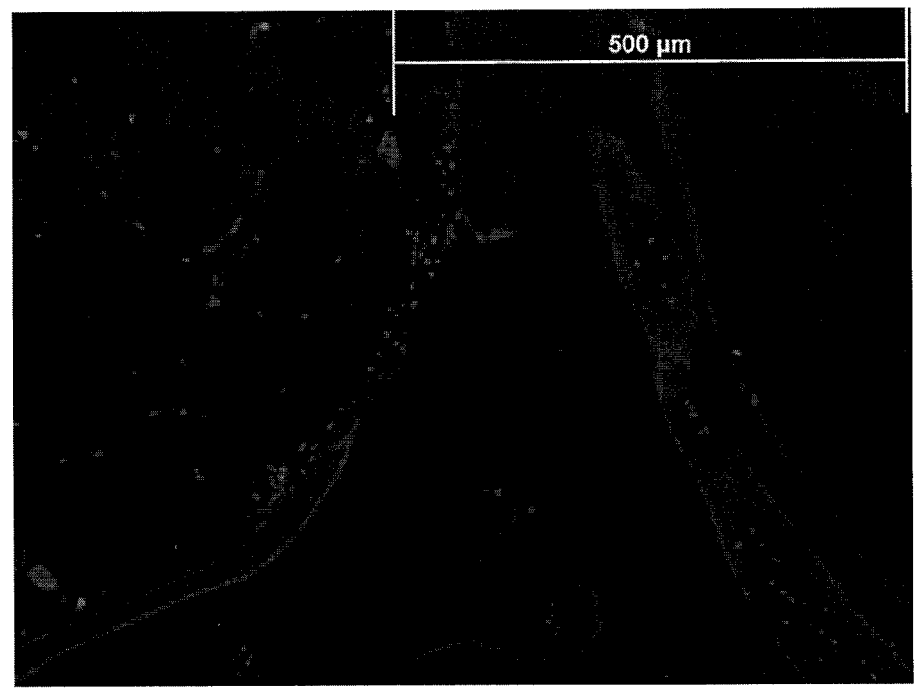

The effect of reduced pressure treatment on induction of endosteal osteogenic activity was evaluated. Contralateral sheep metacarpal bones were used. The dye procion red (0.8%) was introduced into the cannulated median arteries of the bones for 10 minutes. One bone was also subjected to reduced pressure (−125 mm Hg). The contralateral bone was not subjected to reduced pressure. After the treatment, the bones were fixed in 80% ethyl alcohol then subjected to fluoromicroscopy through a green filter. FIG. 11 shows the results. The bone treated with reduced pressure (Panel A) showed much greater circulation of the endosteal surface (as measured by intensity of procion red staining) than the untreated bone (Panel B), indicating increased fluid flow by reduced pressure, even though therapy was applied to the outer periosteal surface.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A system for activating osteogenic or chondrogenic activity at a tissue site in a subject, the system comprising:
   a source of reduced pressure; and
   a manifold formed from an open-cell reticulated foam having pore sizes between about 400 microns and about 600 microns and adapted to be fluidly connected to the source and positioned adjacent dura mater for applying reduced pressure to the dura mater of the subject adjacent the tissue site in the subject;
   wherein the manifold is porous and formed from a flowable material that is deliverable through a manifold delivery tube to the tissue site such that the flowable material is adapted to fill the defect.

2. The system of claim 1, wherein the manifold includes a biocompatible scaffold.

3. The system of claim 2, wherein the biocompatible scaffold is a bioresorbable polymer.

4. The system of claim 3, wherein the bioresorbable polymer is a polylactide-coglycolide (PLAGA) polymer or a polyethylene glycol-PLAGA copolymer.

5. The system of claim 1, wherein the tissue site is a bone or cartilage defect adjacent to the dura mater.

6. The system of claim 5, wherein the defect is (a) from a wound, (b) due to cancer, (c) due to a degenerative disease, or (d) congenital.

7. The system of claim 5, wherein a biocompatible scaffold is inserted into the defect.

8. The system of claim 7, wherein the biocompatible scaffold is a bioresorbable polymer.

9. The system of claim 8, wherein the bioresorbable polymer is a polylactide-coglycolide (PLAGA) polymer or a polyethylene glycol-PLAGA copolymer.

10. The system of claim 1, wherein the reduced pressure induces endosteum osteogenic activity.

11. The system of claim 1, wherein the manifold is a porous, bioresorbable polymer capable of serving as a biocompatible scaffold.

12. The system of claim 1, wherein the reduced pressure is applied for a period of time between about 12 hours and about 3 days.

13. A system for treating a bone or cartilage defect in a subject, the system comprising:
a source of reduced pressure;
a manifold formed from an open-cell reticulated foam having pore sizes between about 400 microns and about 600 microns, fluidly connected to the source and adapted to be positioned adjacent dura mater for applying reduced pressure to the dura mater that is adjacent the defect; and
a biocompatible scaffold configured to be inserted into the defect, the biocompatible scaffold formed of a bioresorable polymer having a polylactide-coglycolide (PLAGA) polymer or a polyethylene glycol-PLAGA copolymer.

14. The system of claim 13, wherein the manifold is porous and formed from a flowable material that is delivered through a manifold delivery tube to the defect such that the flowable material fills the defect.

15. The system of claim 13, wherein the manifold is a porous, bioresorbable polymer capable of serving as a biocompatible scaffold.

16. A system for treating a bone or cartilage defect in a subject, the system comprising:
a source of reduced pressure;
a biocompatible scaffold adapted to be positioned into the defect, the biocompatible scaffold formed of a bioresorable polymer having a polylactide-coglycolide (PLAGA) polymer or a polyethylene glycol-PLAGA copolymer; and
a manifold formed from an open-cell reticulated foam having pore sizes between about 400 microns and about 600 microns and adapted to be fluidly connected to the source of reduced pressure and positioned adjacent dura mater for applying reduced pressure to the dura mater adjacent the defect;
wherein the manifold is porous and formed from a flowable material that is deliverable through a manifold delivery tube to the tissue site such that the flowable material is adapted to fill the defect.

* * * * *